US011864831B2

United States Patent
Inoue et al.

(10) Patent No.: US 11,864,831 B2
(45) Date of Patent: Jan. 9, 2024

(54) VISUAL FIELD TEST DEVICE, METHOD OF CONTROLLING SAME, AND VISUAL FIELD TEST PROGRAM

(71) Applicant: CREWT MEDICAL SYSTEMS, INC., Tokyo (JP)

(72) Inventors: Satoshi Inoue, Tokyo (JP); Shinji Kimura, Tokyo (JP); Kenzo Yamanaka, Tokyo (JP)

(73) Assignee: CREWT MEDICAL SYSTEMS, INC., Tokyo (JP)

( * ) Notice: Subject to any disclaimer, the term of this patent is extended or adjusted under 35 U.S.C. 154(b) by 758 days.

(21) Appl. No.: 16/982,755

(22) PCT Filed: Mar. 6, 2019

(86) PCT No.: PCT/JP2019/008928
§ 371 (c)(1),
(2) Date: Sep. 21, 2020

(87) PCT Pub. No.: WO2019/181517
PCT Pub. Date: Sep. 26, 2019

(65) Prior Publication Data
US 2021/0007598 A1 Jan. 14, 2021

(30) Foreign Application Priority Data
Mar. 19, 2018 (JP) .................. 2018-051554

(51) Int. Cl.
*A61B 3/024* (2006.01)
*G16H 10/60* (2018.01)
(Continued)

(52) U.S. Cl.
CPC .............. *A61B 3/024* (2013.01); *G06N 7/01* (2023.01); *G16H 10/60* (2018.01); *G16H 50/20* (2018.01)

(58) Field of Classification Search
CPC .......... A61B 3/024; G06N 7/01; G16H 10/60; G16H 50/20
(Continued)

(56) References Cited

U.S. PATENT DOCUMENTS 5,461,435 A 10/1995 Rootzen et al.
8,500,278 B2 * 8/2013 Lo ......................... A61B 3/113
351/209
(Continued)

FOREIGN PATENT DOCUMENTS

JP H08-508435 A 9/1996
JP 2008-36295 A 2/2008
(Continued)

OTHER PUBLICATIONS

May 14, 2019 Search Report issued in International Patent Application No. PCT/JP2019/008928.
(Continued)

*Primary Examiner* — Tuyen Tra
(74) *Attorney, Agent, or Firm* — Oliff PLC (57) ABSTRACT

A visual field test device includes: first probability density function acquisition unit performs step (1) of obtaining a probability density function f(x1) for a result value x1 obtained in a first visual field test; a stimulation threshold determination unit performs step (2) of setting a stimulation threshold t1 to a value in the range of x1 in the f(x1); a test result acquisition unit performs step (3) of obtaining test results indicating if a result greater than or equal to t1 was obtained in the first visual field test; a second probability density function acquisition unit performs step (4) of obtaining a probability density function f(x2) by removing probability density values that's greater than or equal to t1, or removing values that are less than t1 from f(x1); and a determination unit performs step (5) of determining if a
(Continued)

standard deviation σ of the f(x2) is below a predetermined value.

12 Claims, 7 Drawing Sheets

(51) Int. Cl.
    *G16H 50/20*     (2018.01)
    *G06N 7/01*     (2023.01)

(58) Field of Classification Search
    USPC .......................................... 351/200, 222, 224
    See application file for complete search history.

(56) References Cited

U.S. PATENT DOCUMENTS

| | | | |
|---|---|---|---|
| 10,631,722 B2 * | 4/2020 | Asaoka | ................ A61B 3/024 |
| 2008/0036966 A1 | 2/2008 | Shimada | |
| 2016/0015263 A1 | 1/2016 | Asaoka et al. | |
| 2018/0153393 A1 | 6/2018 | Asaoka et al. | |

FOREIGN PATENT DOCUMENTS

| | | |
|---|---|---|
| JP | 2014-166250 A | 9/2014 |
| JP | 2016-220832 A | 12/2016 |

OTHER PUBLICATIONS

Turpin, Andrew et al., "Properties of Perimetric Threshold Estimates from Full Threshold, ZEST, and SITA-like Strategies, as Determined by Computer Simulation", Investigative Ophthalmology & Visual Science, Nov. 2003 , vol. 44, pp. 4787-4795.

Tyrpin, Andrew et al., "Development of Efficient Threshold Strategies for Frequency Doubling Technology Perimetry Using Computer Simulation", Investigative Ophthalmology & Visual Science, Feb. 2002, vol. 43, pp. 322-331.

Sep. 22, 2020 International Preliminary Report on Patentability issued in International Patent Application No. PCT/JP2019/008928.

* cited by examiner

FIG. 1

(1) FIRST PROBABILITY DENSITY FUNCTION ACQUIRING STEP
(2) STIMULATION THRESHOLD DETERMINING STEP
(3) TEST RESULT ACQUIRING STEP
(4) SECOND PROBABILITY DENSITY FUNCTION ACQUIRING STEP
(5) DETERMINING STEP (STANDARD DEVIATION σ LESS THAN PREDETERMINED VALUE?)

a = PROBABILITY DENSITY FUNCTION FOR 40 Y.O. AT COORDINATES [−27,−3]
b = PROBABILITY DENSITY FUNCTION FOR 70 Y.O. AT COORDINATES [−27,−3]

a = PROBABILITY DENSITY FUNCTION FOR 40 Y.O. AT COORDINATES [−27,−3]
b = PROBABILITY DENSITY FUNCTION FOR 40 Y.O. AT COORDINATES [−9,−3]

FIG. 5 a = PROBABILITY DENSITY FUNCTION FOR 40 Y.O. AT COORDINATES [−27,−3]
b = PROBABILITY DENSITY FUNCTION AFTER FIRST RESPONSE
c = PROBABILITY DENSITY FUNCTION AFTER SECOND RESPONSE
d = PROBABILITY DENSITY FUNCTION AFTER THIRD RESPONSE

FIG. 6

FIG. 7 a = PROBABILITY DENSITY FUNCTION FOR 40 Y.O. AT COORDINATES [−27,−3]
b = PROBABILITY DENSITY FUNCTION AFTER FIRST RESPONSE
c = PROBABILITY DENSITY FUNCTION AFTER SECOND RESPONSE
d = PROBABILITY DENSITY FUNCTION AFTER THIRD RESPONSE

FIG. 8

VISUAL FIELD TEST DEVICE, METHOD OF CONTROLLING SAME, AND VISUAL FIELD TEST PROGRAM

TECHNICAL FIELD

The present invention relates to a visual field test device, a method of controlling the same, and a visual field test program.

BACKGROUND ART

Technology is known in which, when performing a type of visual field test that is different from the type of visual field test that was performed in the past, sensitivity distribution data of the past visual field test is used in order to calculate the initial luminance of an indicator at corresponding visual field coordinates in the planned visual field test, and the initial luminance is determined as a luminance whose value is equivalent or close to the sensitivity indicated by the sensitivity distribution data (claim 1 of Patent Document 1).

CITATION LIST

Patent Documents

Patent Document 1: JP 2008-36295A

SUMMARY OF INVENTION

Technical Problem

The problem addressed in Patent Document 1 is the ability to efficiently perform a different visual field test. However, this technology is also useful in shortening the time required for one type of visual field test in the first place. It is also very important to obtain accurate test values with a shortened test time.

In view of this, an object of the present invention is to provide a visual field test device, a method of controlling the same, and a visual field test program that can shorten the time required for a visual field test while also obtaining accurate test values.

Solution to Problem

In both the screening test and the threshold test described in Patent Document 1, a predetermined value that has been set in advance is used as the difference between the luminance (hereinafter, in units of dB) of the visual target in the first visual field test and the luminance of the visual target in the second visual field test.

The inventors of the present invention arrived at a technique of determining the luminance of the visual target in the first and subsequent visual field tests based on data (hereinafter, also called "big data") accumulated from visual field tests performed on subjects other than the current test subject.

More specifically, the inventors of the present invention arrived at a technique of determining a test condition for a test subject based on big data. In other words, the inventors arrived at a technique of determining an end condition for test convergence based on a result value obtained in the first visual field test that is actually performed as well as big data.

The following are aspects of the present invention achieved based on the foregoing knowledge.

A first aspect is
a visual field test device including:
a first probability density function acquisition unit configured to perform a step (1) of obtaining a probability density function $f(x1)$ for a result value x1 obtained in a first visual field test, the probability density function $f(x1)$ being a probability density function under at least two conditions regarding a test subject from among the number of years since a last test, an age, test coordinates, a history of illness, an illness name, an disease stage, an estimated threshold used in a past visual field test, and an indicator of a reliability of a past visual field test result;
a stimulation threshold determination unit configured to perform a step (2) of setting a stimulation threshold t1 to a value in a range of x1 in the probability density function $f(x1)$;
a test result acquisition unit configured to perform a step (3) of obtaining a test result indicating whether or not a result greater than or equal to t1 was obtained in the first visual field test;
a second probability density function acquisition unit configured to perform a step (4) of, if a test result greater than or equal to t1 is obtained, obtaining a probability density function $f(x2)$ by removing probability density values that are less than t1 from the probability density function $f(x1)$, and if a test result greater than or equal to t1 is not obtained, obtaining the probability density function $f(x2)$ by removing probability density values that are greater than or equal to t1 from the probability density function $f(x1)$; and
a determination unit configured to perform a step (5) of determining whether or not a standard deviation $\sigma$ of the probability density function $f(x2)$ has fallen below a predetermined value,
wherein if the determination unit determines that the standard deviation $\sigma$ has fallen below the predetermined value, a value of x2 having a highest probability density in the probability density function $f(x2)$ is deemed to be a test value, and testing is ended, and
if the determination unit determines that the standard deviation $\sigma$ has not fallen below the predetermined value, the first visual field test is replaced with a second visual field test, x2 is replaced with x3, x1 is replaced with x2, the stimulation threshold t1 is replaced with a stimulation threshold t2, and the second probability density function acquiring step is replaced with a third probability density function acquiring step, and the stimulation threshold determination unit, the test result acquisition unit, the second probability density function acquisition unit, and the determination unit repeat the steps (2), (3), (4), and (5) until the standard deviation $\sigma$ of a probability density function $f(x3)$ obtained by removing probability density values according to a test result has fallen below the predetermined value.

In a second aspect that is an aspect of the first aspect,
the test result acquisition unit is a perimeter.

In a third aspect that is an aspect of the first or second aspect,
in the second probability density function acquisition unit, probability density values are removed by multiplying the probability density function $f(x1)$ by a response function.

In a fourth aspect that is an aspect of any of the first to third aspects,
the predetermined value used in the determination performed by the determination unit regarding the standard deviation $\sigma$ is a value in a range of 1.0 to 3.5 dB.

A fifth aspect is a method of controlling a visual field test device, including:

a first probability density function acquiring step (1) of obtaining a probability density function f(x1) for a result value x1 obtained in a first visual field test, the probability density function f(x1) being a probability density function under at least two conditions regarding a test subject from among the number of years since a last test, an age, test coordinates, a history of illness, an illness name, an disease stage, an estimated threshold used in a past visual field test, and an indicator of a reliability of a past visual field test result;

a stimulation threshold determining step (2) of setting a stimulation threshold t1 to a value in a range of x1 in the probability density function f(x1);

a test result acquiring step (3) of obtaining a test result indicating whether or not a result greater than or equal to t1 was obtained in the first visual field test;

a second probability density function acquisition step (4) of, if a test result greater than or equal to t1 is obtained, obtaining a probability density function f(x2) by removing probability density values that are less than t1 from the probability density function f(x1), and if a test result greater than or equal to t1 is not obtained, obtaining the probability density function f(x2) by removing probability density values that are greater than or equal to t1 from the probability density function f(x1); and a determining step (5) of determining whether or not a standard deviation σ of the probability density function f(x2) has fallen below a predetermined value, wherein if it is determined in the step (5) that the standard deviation σ has fallen below the predetermined value, a value of x2 having a highest probability density in the probability density function f(x2) is deemed to be a test value, and testing is ended, and if it is determined in the step (5) that the standard deviation σ has not fallen below the predetermined value, the first visual field test is replaced with a second visual field test, x2 is replaced with x3, x1 is replaced with x2, the stimulation threshold t1 is replaced with a stimulation threshold t2, and the second probability density function acquiring step is replaced with a third probability density function acquiring step, and a stimulation threshold determination unit, a test result acquisition unit, a second probability density function acquisition unit, and a determination unit repeat the steps (2), (3), (4), and (5) until the standard deviation σ of a probability density function f(x3) obtained by removing probability density values according to a test result has fallen below the predetermined value.

In a sixth aspect that is an aspect of the fifth aspect, the steps (2), (3), (4), and (5) are performed three times or fewer.

In a seventh aspect that is an aspect of the fifth or sixth aspect, in the step (4), probability density values are removed by multiplying the probability density function f(x1) by a response function.

In an eighth aspect that is an aspect of any of the fifth to seventh aspects, the predetermined value used in the determination performed in the step (5) regarding the standard deviation σ is a value in a range of 1.0 to 3.5 dB.

A ninth aspect is a visual field test program that causes a computer device to function as:

a first probability density function acquisition unit configured to perform a step (1) of obtaining a probability density function f(x1) for a result value x1 obtained in a first visual field test, the probability density function f(x1) being a probability density function under at least two conditions regarding a test subject from among the number of years since a last test, an age, test coordinates, a history of illness, an illness name, an disease stage, an estimated threshold used in a past visual field test, and an indicator of a reliability of a past visual field test result;

a stimulation threshold determination unit configured to perform a step (2) of setting a stimulation threshold t1 to a value in a range of x1 in the probability density function f(x1);

a test result acquisition unit configured to perform a step (3) of obtaining a test result indicating whether or not a result greater than or equal to t1 was obtained in the first visual field test;

a second probability density function acquisition unit configured to perform a step (4) of, if a test result greater than or equal to t1 is obtained, obtaining a probability density function f(x2) by removing probability density values that are less than t1 from the probability density function f(x1), and if a test result greater than or equal to t1 is not obtained, obtaining the probability density function f(x2) by removing probability density values that are greater than or equal to t1 from the probability density function f(x1); and a determination unit configured to perform a step (5) of determining whether or not a standard deviation σ of the probability density function f(x2) has fallen below a predetermined value, wherein if the determination unit determines that the standard deviation σ has fallen below the predetermined value, a value of x2 having a highest probability density in the probability density function f(x2) is deemed to be a test value, and testing is ended, and if the determination unit determines that the standard deviation σ has not fallen below the predetermined value, the first visual field test is replaced with a second visual field test, x2 is replaced with x3, x1 is replaced with x2, the stimulation threshold t1 is replaced with a stimulation threshold t2, and the second probability density function acquiring step is replaced with a third probability density function acquiring step, and the stimulation threshold determination unit, the test result acquisition unit, the second probability density function acquisition unit, and the determination unit repeat the steps (2), (3), (4), and (5) until the standard deviation σ of a probability density function f(x3) obtained by removing probability density values according to a test result has fallen below the predetermined value.

In a tenth aspect that is an aspect of the ninth aspect, the steps (2), (3), (4), and (5) are performed three times or fewer.

In an eleventh aspect that is an aspect of the ninth or tenth aspect, in the step (4), probability density values are removed by multiplying the probability density function f(x1) by a response function.

In a twelfth aspect that is an aspect of any of the ninth to eleventh aspects, the predetermined value used in the determination performed in the step (5) regarding the standard deviation σ is a value in a range of 1.0 to 3.5 dB.

Advantageous Effects of Invention

According to the present invention, it is possible to provide a visual field test device, a method of controlling the same, and a visual field test program that can shorten the time required for a visual field test while also obtaining accurate test values.

BRIEF DESCRIPTION OF DRAWINGS

FIG. 2(*a*) is a plot of a probability density function f(x1) in the case where "Age: 40" and "Test coordinates: [−27,−3]" were selected. FIG. 2(*b*) is a plot of the probability density function f(x1) in the case where "Age: 70" and "Test coordinates: [−27,−3]" were selected.

FIG. 3(*a*) is a plot of the probability density function f(x1) in the case where "Age: 40" and "Test coordinates: [−27,−3]" were selected. FIG. 3(*b*) is a plot of the probability density function f(x1) in the case where "Age: 40" and "Test coordinates: [−9,−3]" were selected.

FIG. 4(*a*) is a plot of the probability density function f(x1) in the case where "Age: 40", "Test coordinates: [−27,−3]", and "History of glaucoma: no" were selected. FIG. 4(*b*) is a plot of the probability density function f(x1) in the case where "Age: 40", "Test coordinates: [−27,−3]", and "History of glaucoma: yes (ongoing)" were selected.

FIG. 5(*a*) is a plot of the probability density function f(x1) in the case where "Age: 40" and "Test coordinates: [−27,−3]" were selected. FIG. 5(*b*) is a plot of a probability density function f(x2) after a first visual field test in Working Example 1. FIG. 5(*c*) is a plot of a probability density function f(x3) after a second visual field test in Working Example 1. FIG. 5(*d*) is a plot of a probability density function f(x4) after a third visual field test in Working Example 1.

FIG. 7(*a*) is a plot of the probability density function f(x1) in the case where "Age: 40" and "Test coordinates: [−27,−3]" were selected in Working Example 2. FIG. 7(*b*) is a plot of the probability density function f(x2) after a first visual field test in Working Example 2. FIG. 7(*c*) is a plot of the probability density function f(x3) after a second visual field test in Working Example 2. FIG. 7(*d*) is a plot of the probability density function f(x4) after a third visual field test in Working Example 2.

FIG. 8(*a*) is a plot of the probability density function f(x1) in the case where "Age: 40", "Test coordinates: [−27,−−3]", and "History of glaucoma: yes (ongoing)" were selected in Working Example 3. FIG. 8(*b*) is a plot of the probability density function f(x2) after a first visual field test in Working Example 3. FIG. 8(*c*) is a plot of the probability density function f(x3) after a second visual field test in Working Example 3.

DESCRIPTION OF EMBODIMENTS

The following is a detailed description of an embodiment of the present invention with reference to the drawings.

The present embodiment will be described in the order shown below. Note that the symbol "~" represents being greater than or equal to a predetermined numerical value and less than or equal to a predetermined numerical value.

1. Visual Field Test Device
   1-1. First probability density function acquisition unit
   1-2. Stimulation threshold determination unit
   1-3. Test result acquisition unit
   1-4. Second probability density function acquisition unit
   1-5. Determination unit
2. Method of controlling visual field test device
3. Visual field test program
4. Effects of embodiment
5. Variations etc.

Note that configurations of a known visual field test device may be used for configurations that are not described below. For example, it is possible to appropriately apply configurations described in JP 5826902B held by the applicant of the present invention, or configurations described in JP 2017-192564A likewise submitted by the applicant of the present invention. Note that the visual field test device may be an HMD (head-mounted display) device that is connected to a control computer unit, or may be a stationary device.

Figure 1:
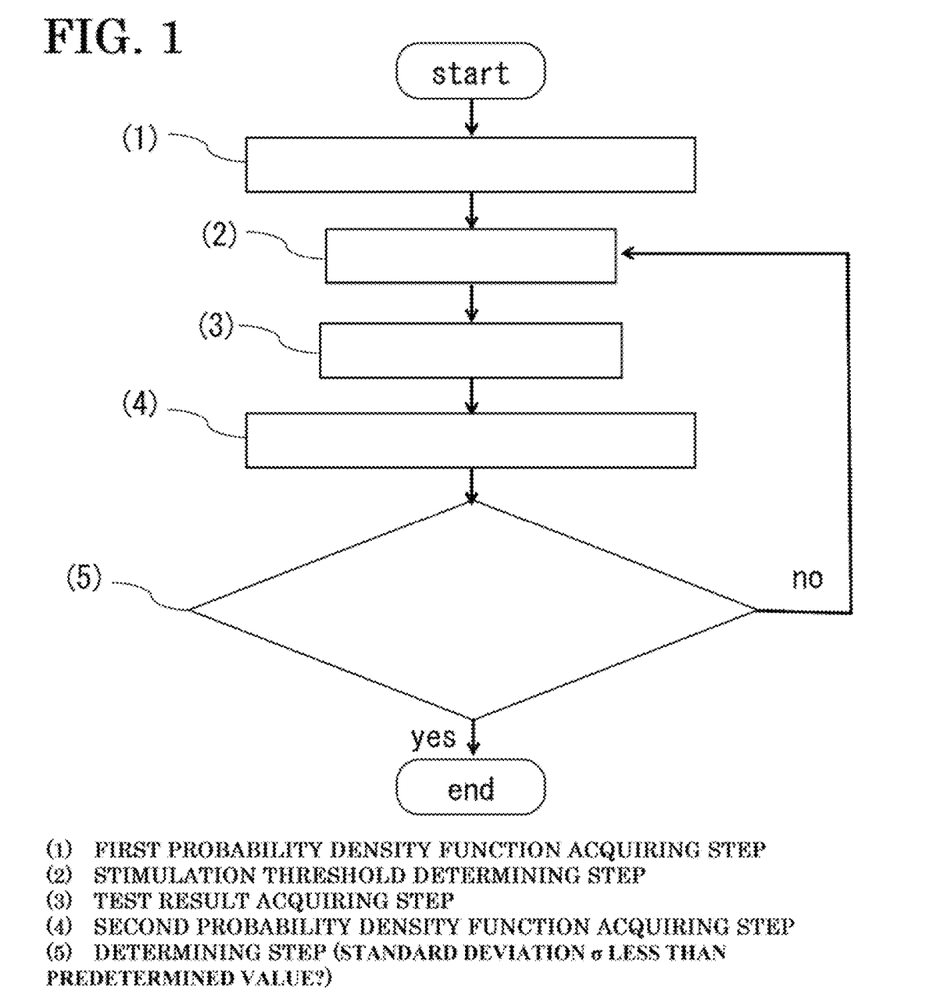
FIG. 1 is a flowchart showing steps performed by units in a visual field test device according to an embodiment of the present invention (i.e., shows a method of controlling the visual field test device).

FIG. 1 is a flowchart showing steps performed by units in a visual field test device according to the present embodiment (i.e., shows a method of controlling the visual field test device). The following description is given with reference to FIG. 1.

1. Visual Field Rest Device

1-1. First Probability Density Function Acquisition Unit

A first probability density function acquiring step (1) is performed by a first probability density function acquisition unit. This is a step for obtaining a probability density function f(x1) for a result value x1 obtained in a first visual field test. This probability density function f(x1) is obtained under at least two conditions from the items listed below.

Number of years since test subject's last test
Age
Test coordinates
History of illness
Illness
Disease stage
Estimated threshold in past visual field test
Indicator of reliability of past visual field test result Here, "Number of years since test subject's last test" is self-explanatory, that is to say the number of years since the last visual field test was performed. Also, "Age" is self-explanatory.

Also, "Test coordinates" refers to the test point used in the screening test and the threshold test described in Patent Document 1, and is a point that has a predetermined luminance. This test point is presented to the test subject as a visual target. Note that the visual target in the present embodiment is displayed in order to perform the visual field test, and there are no particular limitations on the visual target.

Also, "History of illness" is self-explanatory, that is to say indicates whether or not the test subject is suffering from (or has suffered from) glaucoma, for example. Also, "Illness" is self-explanatory, and one example is glaucoma. Here, "History of illness" and "Illness" may be combined into the item "History of glaucoma". Also, "Disease stage" means the extent of the progression of glaucoma, for example.

The following describes the condition "Estimated threshold in past visual field test".

In conventional visual field tests, one test value is obtained at the end of one test. However, the test value is merely an estimate value, and the status of the test subject is approximately reflected in the value, not completely reflected. This point also similarly applies to the test value that is ultimately obtained in the present embodiment.

For this reason, in the present specification, the term "estimated threshold" refers to one test value obtained at the end of a test performed using the visual field test device of the present embodiment (and the value of x used in the determination of the predetermined value that is a standard deviation σ in a determining step (5) described in detail later), as well as one test value obtained at the end of a conventional visual field test.

In the case of applying the estimated threshold item that was used in a past visual field test, the probability density function is obtained as described below.

Figure 2:
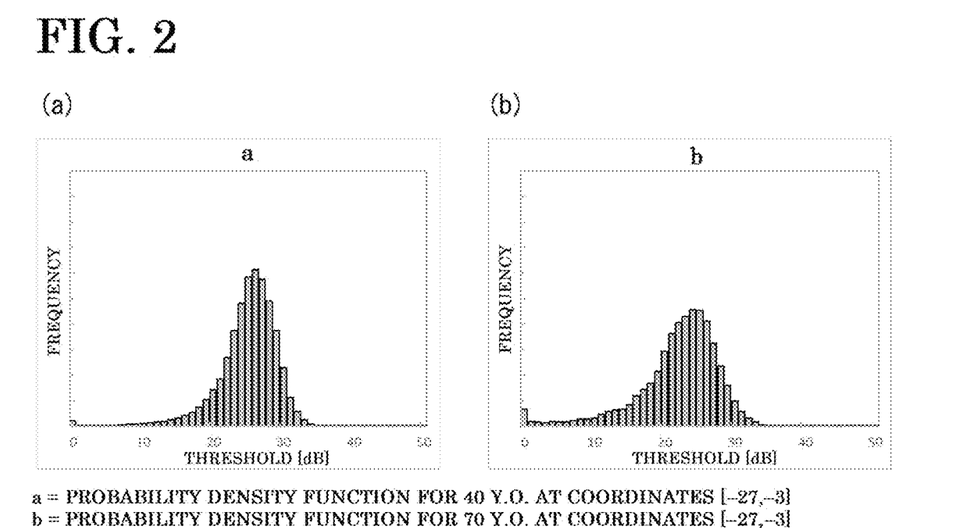

For example, envision the case of a sample where a 21 dB visual target is recognized, and then a 27 dB visual target is recognized in the next visual field test. That past estimated threshold is added to the number of samples corresponding to 27 dB on the horizontal axis of the probability density function for the case of 21 dB (e.g., a plot formatted as shown in FIG. 2(a)). By incrementing the number of samples in this way, a probability density function for the case of 21 dB is obtained from estimated thresholds that were used in past visual field tests.

Note that in the present specification, a higher test value (dB) in a visual field test indicates that the test subject recognized a darker visual target (i.e., the test subject has a good visual field), whereas a lower value indicates that the test subject did not recognize a brighter visual target (i.e., the test subject has a poor visual field).

Also, "Indicator of reliability of past visual field test result" refers to the reliability visual target described in JP 2017-192564A submitted by the applicant of the present invention. In the present specification, the reliability indicator is an indicator of how high the reliability is, and is a result obtained based on the number of normally improbable responses under numerical conditions that are different from the test result.

The reliability visual target is described in JP 2017-192564A. The entirety of the description of the reliability indicator in JP 2017-192564A will serve as the description of the reliability indicator in the present specification.

The following describes big data. The big data used in the present embodiment is, for example, accumulated data pertaining to various test subjects that has been input to visual field test devices. This big data may be acquired from a server at a different location via a communication line. Note that representative data may be prepared for the above-described items instead of big data or for use at a stage before data has been accumulated.

The following describes a concrete example of using big data in this step. When the test subject starts the visual field test, "Age: 40" and "Test coordinates: [−27,−3]" are selected from among the above-described items.

Accordingly, data that matches the conditions "Age: 40" and "Test coordinates: [−27,−3]" is extracted from big data accumulated through visual field tests performed at various locations. The extracted data is used as a basis for calculating data regarding whether or not various test subjects who satisfy the two aforementioned conditions could recognize visual targets with various luminance values when visual field tests were performed. A first probability density function having the threshold (dB) as one variable (the horizontal axis of the plot) and having the frequency (i.e., the probability density) as another variable (the vertical axis of the plot) is then created and acquired.

FIG. 2(a) is a plot of a probability density function f(x1) in the case where "Age: 40" and "Test coordinates: [−27,−3]" were selected.

FIG. 2(b) is a plot of the probability density function f(x1) in the case where "Age: 70" and "Test coordinates: [−27,−3]" were selected.

Similarly, in the case of other items as well, data that matches the selected combination of two or more conditions is extracted from big data accumulated through visual field tests performed at various locations. The extracted data is used as a basis for calculating data regarding whether or not various test subjects who satisfy the selected conditions could recognize visual targets with various luminance values when visual field tests were performed. A first probability density function having the threshold (dB) as the horizontal axis and having the frequency as the vertical axis is then created and acquired.

Figure 3:
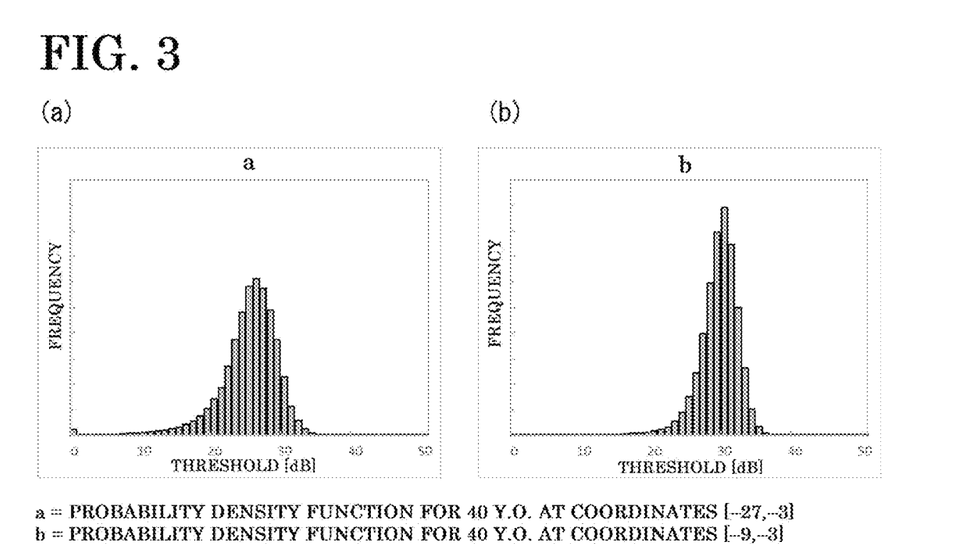

FIG. 3(a) is a plot of the probability density function f(x1) in the case where "Age: 40" and "Test coordinates: [−27,−3]" were selected. FIG. 3(a) is the same as FIG. 2(a), but is reused to facilitate a comparison with FIG. 3(b).

FIG. 3(b) is a plot of the probability density function f(x1) in the case where "Age: 40" and "Test coordinates: [−9,−3]" were selected.

Figure 4:
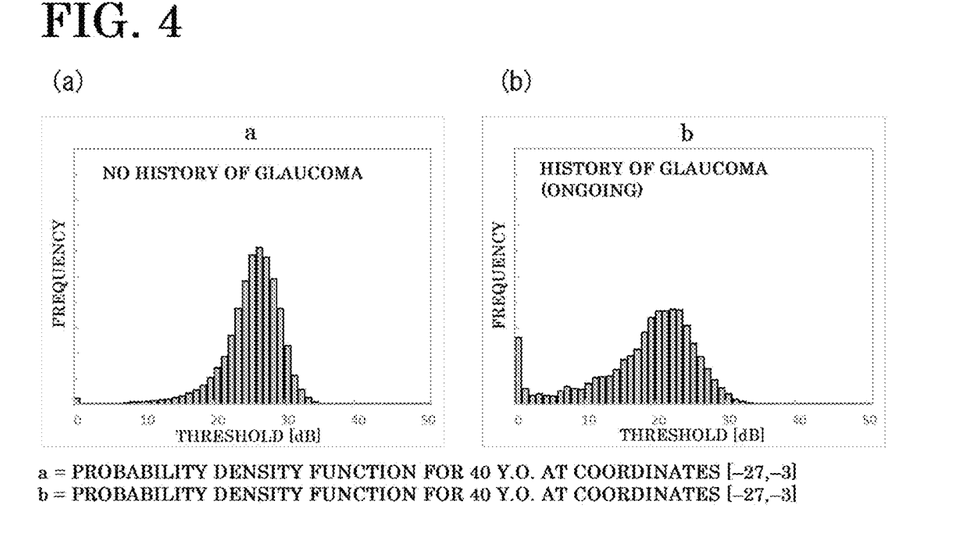

FIG. 4(a) is a plot of the probability density function f(x1) in the case where "Age: 40", "Test coordinates: [−27,−3]", and "History of glaucoma: no" were selected.

FIG. 4(b) is a plot of the probability density function f(x1) in the case where "Age: 40", "Test coordinates: [−27,−3]", and "History of glaucoma: yes (ongoing)" were selected.

Note that the horizontal axis of the plot is labeled as simply "threshold" rather than "estimated threshold" for a reason. The reason for this is described below.

In the present embodiment, there is also a "stimulation threshold" that is different from the estimated threshold that is ultimately obtained as the test value. The "stimulation threshold" is the luminance applied as the visual target of the visual field test when performing a later-described test result acquiring step (3), that is to say the step for acquiring the result of the visual field test.

Although described in more detail later, in a stimulation threshold determining step (2), a stimulation threshold t1, that is to say the luminance of the visual target that is to be applied in the test result acquiring step (3), is set to a value in the range of x1 in the probability density function f(x1). For this reason, the thresholds on the horizontal axes of the plots in FIGS. 2(a) and 2(b) are values that can serve as the stimulation threshold U.

On the other hand, the horizontal axis of the plot of a probability density function f(x2) obtained in a later-described second probability density function acquiring step (4) indicates the estimated threshold in some cases and the stimulation threshold in other cases.

In a determining step (5), if it is determined that the standard deviation σ is less than a predetermined value and the test is to end, a value x2 having the highest probability density serves as the ultimately obtained test value, that is to say the estimated threshold. Conversely, if the standard deviation σ is greater than or equal to the predetermined value, the stimulation threshold determining step (2) is performed again based on the probability density function f(x2). In this case, the horizontal axis of the plot of the probability density function f(x2) indicates the stimulation threshold.

More specifically, depending on the result of the determining step (5), the horizontal axis of the plot of the probability density function f(x2) indicates the estimated threshold in some cases and indicates the stimulation threshold in other cases, and therefore is simply labeled as "threshold". Note that this does not exclude the case where a stimulation threshold used in a past visual field test is applied as an item in the first probability density function acquiring step (1).

The above description pertains to the processing performed in the present step, and this content is a function realized by the first probability density function acquisition unit.

1-2. Stimulation Threshold Determination Unit

A stimulation threshold determining step (2) is performed by the stimulation threshold determination unit. In this step, the stimulation threshold t1 is set to a value in the range of x1 in the probability density function f(x1).

Here, "the range of x1 in the probability density function f(x1)" refers to the range of x1 from the smallest value at which the probability density exists to the largest value at which the probability density exists. This corresponds to the range of 0 to 34 dB in FIG. 2(a). According to this expression, x1 having a probability density of 0 may exist in the range.

According to this configuration, when a later-described second probability density function acquiring step (4) is performed, unnecessary probability density values (i.e., probability density values that are greater than or equal to the stimulation threshold t1, or probability density values that are less than t1) are removed. This consequently makes it possible to shorten the time required for the visual field test.

Also, a result value x1 in the range of 10 to 90% of the cumulative probability density (preferably 30 to 70%, more preferably 35 to 65%, and further preferably 40 to 60%) may be set as the stimulation threshold t1.

Note that a random number that satisfies the above-described condition may be set as t1, and a calculation unit may set t1 to a value that minimizes the number of times that the visual field test is performed (described in detail later).

1-3. Test Result Acquisition Unit

A test result acquiring step (3) is performed by a test result acquisition unit. This is a step for obtaining a test result indicating whether or not a result greater than or equal to t1 was obtained in the first visual field test.

More specifically, in this step, a visual target whose luminance is t1 (dB) is presented to the test subject, and a test resulting indicating whether or not the test subject recognized the visual target is obtained.

A perimeter is one example of the test result acquisition unit. Note that besides being configured as a perimeter, a configuration is possible in which, for example, a perimeter is disposed at a remote location, and the test result obtained by the perimeter is acquired by the test result acquisition unit of the visual field test device according to the present embodiment.

1-4. Second Probability Density Function Acquisition Unit

A second probability density function acquiring step (4) is performed by a second probability density function acquisition unit. In this step, if a test result greater than or equal to t1 is obtained, the probability density function f(x2) is obtained by removing the probability density values that are less than t1 from the probability density function f(x1). More specifically, if the test subject could recognize the visual target having the predetermined luminance (here, t1 (dB)), the ultimately obtained test value can be predicted to be greater than or equal to approximately t1 (dB). For this reason, the probability density values less than t1 (dB) in the probability density function f(x1) may be excluded or removed.

On the other hand, if a test result greater than or equal to t1 is not obtained, the probability density function f(x2) is obtained by removing the probability density values that are greater than or equal to t1 from the probability density function f(x1). More specifically, if the test subject could not recognize the visual target having the predetermined luminance (here, t1 (dB)), the ultimately obtained test value can be predicted to be less than approximately t1 (dB). For this reason, the probability density values greater than or equal to t1 (dB) in the probability density function f(x1) may be excluded or removed.

Note that the probability density function f(x2) may be obtained by first excluding or removing probability density values, and then converting the sum probability density of all of the values of x2 to a percentage.

Any specific technique may be used when removing probability density values from the probability density function f(x1). For example, probability density values may be removed by multiplying the probability density function f(x1) by a response function.

For example, according to this response function, in the case of removing probability density values less than t1, x1 values in the probability density function f(x1) that are lower than t1−3 dB may be multiplied by 0, x1 values that are higher than t1+3 dB may be multiplied by 1, and x1 values that are in the range of t1±3 dB may be multiplied by a value that is between −1 and +1 and is approximately linearly proportional.

On the other hand, in the case of removing probability density values greater than or equal to t1, x1 values in the probability density function f(x1) that are lower than t1−3 dB may be multiplied by 1, x1 values that are higher than t1+3 dB may be multiplied by 0, and x1 values that are in the range of t1±3 dB may be multiplied by a value that is between −1 and +1 and is approximately linearly inversely proportional.

Note that the response function used after the second and subsequent visual field tests may be a variation of the above-described response function or a different response function.

For example, as shown in a later-described working example, the response function may be set such that, after the second visual field test, the intersection of the response function in the case of successful recognition and the response function in the case of failed recognition is the stimulation threshold t2 that was applied in the second visual field test (t3 in the case of the third visual field test).

For x1 values in the range of t1±3 dB, it is possible to create the "response function in the case of successful recognition" that has an approximately linearly proportional value between −1 and +1, and create the "response function in the case of failed recognition" that has an approximately inversely linearly proportional between −1 and +1.

Note that the above-described range ±3 dB is merely one example, and this range may be ±1 to 10.

Also, the response function is not limited to the above-described aspect, and need only be to exclude or remove unnecessary probability density values.

Furthermore, instead of multiplying the probability density function f(x1) by a response function, it is possible to remove probability density values that are greater than or equal to the stimulation threshold t1, or are less than t1, while leaving the stimulation threshold t1 remaining. Given that there is a possibility of the test subject mistakenly recognizing the visual target, it is preferable to leave x1 values for which the probability density is close to stimulation threshold t1. It is for this reason that in the probability density function f(x1), x1 values in the range of t1±3 dB are multiplied by an approximately linearly proportional or linearly inversely proportional value between −1 and +1.

1-5. Determination Unit

A determining step (5) is performed by a determination unit. This is a step for determining whether or not the standard deviation σ of the probability density function f(x2) has fallen below a predetermined value.

If the standard deviation σ has fallen below the predetermined value, it is deemed that the value of x2 having the highest probability in the probability density function f(x2) is the test value, and the test is ended. The value of x2 having the highest probability when the standard deviation σ is below the predetermined value has a very high likelihood of being the actual test value of the test subject. For this reason, the time required for the visual field test can be shortened while also obtaining an accurate test value.

The predetermined value may be set appropriately in a range of 0.5 to 10.0 dB, for example. Also, the predetermined value may be set using an equation. For example, in later-described Working Example 1, the predetermined value is set using the following equation.

$$\text{standard deviation } \sigma = \text{abs}(20-x)*(-0.1)+4.0$$

The value of x used in this equation may be the average value of x2 in the probability density function f(x2) that has already been created when the determining step (5) is performed, or may be the median value of x2, or may be the value of x2 having the highest frequency (i.e., having the highest probability density) in order for application in a later-described working example. Also, in order for application in a later-described working example, the predetermined value may be changed according to the value of x2, x3, and x4 each time steps (2), (3), (4), and (5) are repeated. Of course, the predetermined value may be a fixed value.

Note that if x4 is the final test value (estimated threshold), x3 is not the final test value, strictly speaking. However, it remains a value obtained by one test. In view of this, in consideration of the fact that x3 was used when determining the predetermined value that is to be the standard deviation σ, x3 may be deemed to be an "Estimated threshold used in past visual field test" in the first probability density function acquiring step (1), and data indicating that the test value obtained after x3 is x4 may be accumulated as part of the big data. Similarly, x2 may also be deemed to be an "Estimated threshold used in past visual field test", and data indicating that the test value obtained after x2 is x3 may be accumulated as part of the big data. Accordingly, the big data accumulation speed increases, and therefore an even more accurate test value is obtained by using the visual field test device of the present embodiment.

Note that the above-described equation may be modified or replaced in accordance with the items that are applied in the first probability density function acquiring step (1).

On the other hand, if the standard deviation σ has not fallen below the predetermined value, steps (2), (3), (4), and (5) are repeated. The follow replacements are made in the content of steps (2), (3), (4), and (5) when they are repeated.

the first visual field test is replaced with the second visual field test
x2 is replaced with x3
x1 is replaced with x2
the stimulation threshold t1 is replaced with t2
the second probability density function acquiring step is replaced with the third probability density function acquiring step The steps (2), (3), (4), and (5) are repeated in order until it is determined that the standard deviation σ of the probability density function f(x3), from which probability density values have been removed according to the test result, has fallen below the predetermined value. Note that in order to further shorten the time required for testing, it is preferable that the steps (2), (3), (4), and (5) are performed three times or fewer (three rounds or fewer).

Note that it is sufficient that the control of units, including the repetition of the steps (2), (3), (4), and (5), is performed by a control computer unit provided in the visual field test device.

2. Method of Controlling Visual Field Test Device

The technical features of the present invention are also reflected in a method of controlling the visual field test device described in section "1. Visual field test device". More specifically, the effects of the present invention are obtained if the control computer unit of the visual field test device of the present embodiment controls the units described above so as to execute the steps (1), (2), (3), (4), and (5).

3. Visual Field Test Program

The technical features of the present invention are also reflected in a visual field test program executed by a computer device that realizes the visual field test device described in section "1. Visual field test device". More specifically, the visual field test program of the present embodiment is a program for causing a computer device to function as the first probability density function acquisition unit, the stimulation threshold determination unit, the test result acquisition unit, the second probability density function acquisition unit, and the determination unit described above. The content of the determination made by the determination unit is similar to the content described in the section "1. Visual field test device", and therefore will not be described again.

4. Effects of Embodiment

In the present embodiment, an end condition for test convergence is determined based on a result value obtained in the first visual field test that is actually performed and big data.

Accordingly, it is possible to provide a visual field test device, a method of controlling the same, and a visual field test program that can shorten the time required for a visual field test while also obtaining an accurate test value.

5. Variations etc.

The present invention is not limited to the content of the embodiment described above, and appropriate changes can be made without departing from the gist of the invention. Also, the above-described configurations and preferred examples can be combined.

In the present embodiment, the stimulation threshold t1 may be determined in any way as long as the probability density values in the probability density function f(x1) are divided. Note that in order to effectively remove unnecessary probability density values in the step (4), it is possible to separately provide a calculation unit (a program for controlling/executing the same) for performing a calculation step of calculating t1 so as to minimize the number of times the visual field test is performed.

As one specific example, inverse calculation is performed such that the standard deviation σ of the probability density function ultimately falls below the predetermined value (e.g., 1.0 to 3.5 dB). Then a simulation is performed to obtain the number of tests that need to be performed when the stimulation threshold t1 in the first visual field test, the stimulation threshold t2 in the second visual field test, and the stimulation threshold t3 in the third visual field test are set to specific numerical values. The stimulation threshold may then be set to the value that achieves the smallest number of visual field tests from among the simulation results.

In the present embodiment, the probability density function is obtained under at least two conditions from among items such as the number of years since the last test. However, the probability density function may be obtained under at least one condition from among the items. Note that using multiple items makes it possible for the individual situation of the test subject to be further reflected in the stimulation threshold, and obtains a more accurate test value.

In the present embodiment, the case of performing a visual field test is described. However, the present invention is not limited to be applied to a visual field test, and may be applied to any type of visual test that uses some sort of threshold to determine whether or not a visual target can be recognized.

WORKING EXAMPLES

The following describes working examples of the present invention. Note that the technical scope of the present invention is not limited to the working examples described below.

Working Example 1

A test subject A was subjected to a visual field test using an HMD-type of visual field test device of the present embodiment.

The first probability density function acquiring step (1) was performed using the items "Age: 40" and "Test coordinates: [−27,−3]" acquired from information regarding the test subject A.

Figure 5:
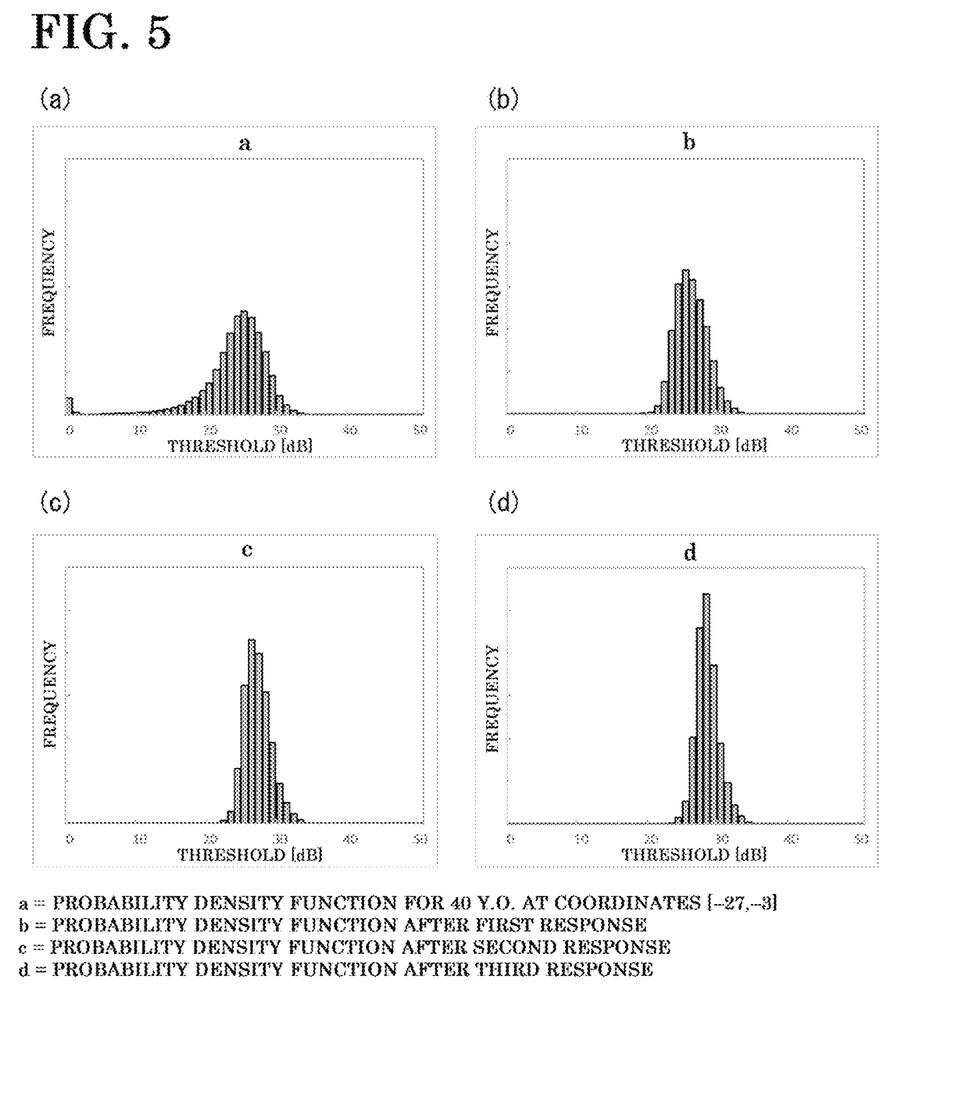

FIG. 5($a$) is a plot of the probability density function f(x1) in the case where "Age: 40" and "Test coordinates: [−27,−−3]" were selected in Working Example 1. FIG. 5($a$) is the same as FIG. 2($a$), but is reused to facilitate a comparison with FIGS. 5($b$) to ($d$).

First Round

The stimulation threshold t1 was set to 21 dB from within the range of x1 in the probability density function f(x1) (stimulation threshold determining step (2)). Note that the value 21 dB is the average value of x1 in the probability density function f(x1). This similarly applies to the subsequent stimulation threshold determining step (2).

Then a perimeter was used to perform the test result acquiring step (3) for obtaining a test result indicating whether or not a result greater than or equal to 21 dB was obtained in the first visual field test. The obtained result indicated that the test subject recognized the visual target.

Because a test result greater than or equal to 21 dB was obtained, in the second probability density function acquiring step (4), the probability density function f(x2) was obtained by removing the probability density values lower than 21 dB from the probability density function f(x1). At this time, the probability density function f(x2) was obtained by first excluding or removing probability density values, and then converting the sum probability density of all of the values of x2 to a percentage. Hereinafter, unless particularly stated otherwise, similar processing is performed after multiplication by the response function.

FIG. 5($b$) is a plot of the probability density function f(x2) after the first visual field test in Working Example 1.

Figure 6:
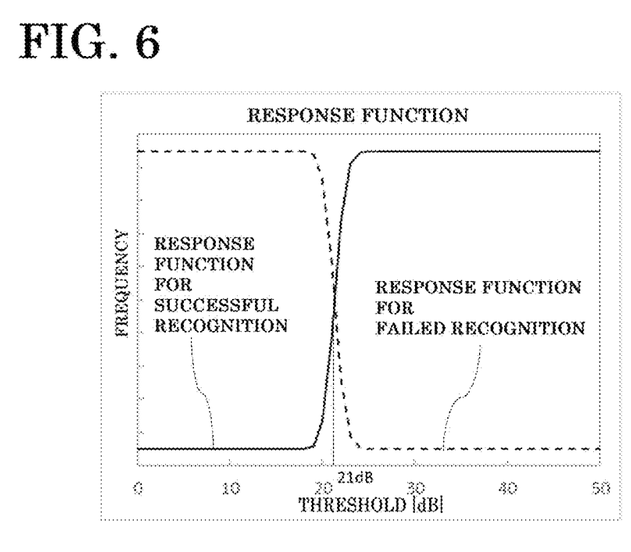
FIG. 6 is a plot of a response function used after the first visual field test in Working Example 1.

Note that when the probability density values were removed from the probability density function f(x1), the probability density function f(x1) was multiplied by the response function for the case of successful recognition shown in FIG. 6.

FIG. 6 is a plot of the response function used after the first visual field test in Working Example 1.

Note that the response function used after the second and subsequent visual field tests in Working Example 1 and the response functions in the other working examples were prepared as described below.

The response function used after the second visual field test in Working Example 1 was set such that the intersection between the response function in the case of successful recognition and the response function in the case of failed recognition is the stimulation threshold t2 (later-described 23 dB) that was applied in the second visual field test.

For x2 in the range of t2±3 dB, in the case of successful recognition, the probability density function f(x2) is multiplied by a response function that is an approximately linearly proportional value between −1 and +1, whereas in the case of failed recognition, the probability density function f(x2) is multiplied by a response function that is an approximately inversely linearly proportional value between −1 and +1.

After the third visual field test in the Working Example 1 and in the other working examples as well, the response function is created using the method described above.

Then the determining step (5) was performed to determine whether or not the standard deviation σ of the probability density function f(x2) had fallen below the predetermined value 3.4 dB (=(−0.1)*abs(20−26)+4.0). It was determined that the standard deviation σ did not fall below 3.4 dB in the first visual field test. The estimated threshold used when obtaining the standard deviation σ, which is a predetermined value, is set to the value of x2 having the highest probability density, that is to say the value of x2 having the highest frequency. This similarly applies hereinafter.

Second Round

The steps (2), (3), (4), and (5) were repeated in order.

More specifically, the stimulation threshold t2 was set to 23 dB from within the range of x2 in the probability density function f(x2) (stimulation threshold determining step (2)).

Then a perimeter was used to perform the test result acquiring step (3) for obtaining a test result indicating whether or not a result greater than or equal to 23 dB was obtained in the second visual field test. The obtained result indicated that the test subject recognized the visual target.

Because a test result greater than or equal to 23 dB was obtained, in the second probability density function acquiring step (4), the probability density function f(x3) was obtained by removing the probability density values lower than 23 dB from the probability density function f(x2).

FIG. 5($c$) is a plot of the probability density function f(x3) after the second visual field test in Working Example 1.

Then the determining step (5) was performed to determine whether or not the standard deviation σ of the probability density function f(x3) had fallen below the predetermined value 3.3 dB (=(−0.1)*abs(20−27)+4.0). It was determined that the standard deviation σ did not fall below 3.3 dB in the second visual field test either.

Third Round

The steps (2), (3), (4), and (5) were again repeated in order.

More specifically, the stimulation threshold t3 was set to 26 dB from within the range of x3 in the probability density function f(x3) (stimulation threshold determining step (2)).

Then a perimeter was used to perform the test result acquiring step (3) for obtaining a test result indicating whether or not a result greater than or equal to 26 dB was obtained in the third visual field test. The obtained result indicated that the test subject recognized the visual target.

Because a test result greater than or equal to 26 dB was obtained, in the second probability density function acquiring step (4), the probability density function f(x4) was obtained by removing the probability density values lower than 26 dB from the probability density function f(x3).

FIG. 5(d) is a plot of the probability density function f(x4) after the third visual field test in Working Example 1.

Then the determining step (5) was performed to determine whether or not the standard deviation σ of the probability density function f(x4) had fallen below the predetermined value 3.1 dB (=(−0.1)*abs(20−29)+4.0). It was then determined that the standard deviation σ had fallen below 3.1 dB. The value of x4 having the highest probability density in the probability density function f(x4) was 29 dB.

The test value ultimately obtained through the above steps was 29 dB, and the visual field test was then ended.

Working Example 2

A test subject B was subjected to a visual field test using the visual field test device of the present embodiment.

Similarly to Working Example 1, the first probability density function acquiring step (1) was performed using the items "Age: 40" and "Test coordinates: [−27,−3]" acquired from information regarding the test subject B.

Figure 7:
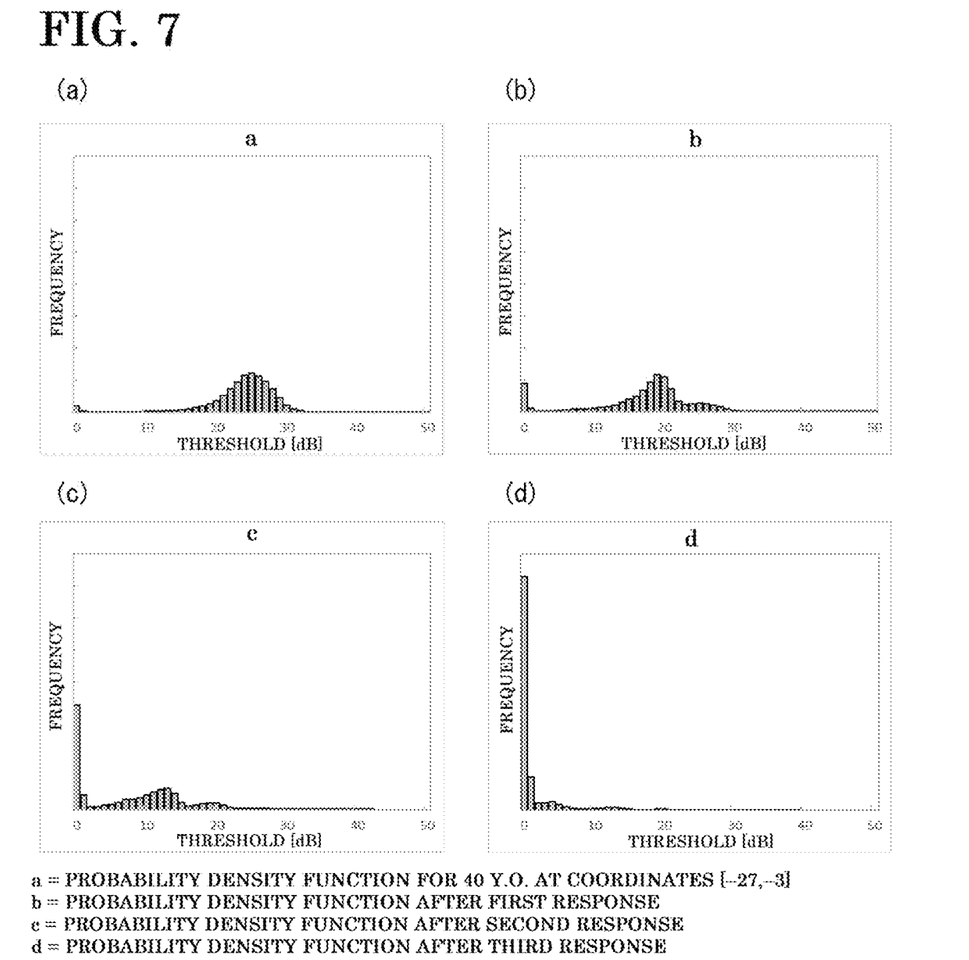

FIG. 7(a) is a plot of the probability density function f(x1) in the case where "Age: 40" and "Test coordinates: [−27,−3]" were selected in Working Example 2. FIG. 7(a) is the same as FIG. 2(a), but is reused to facilitate a comparison with FIGS. 7(b) to (d).

First Round

The stimulation threshold t1 was set to 21 dB from within the range of x1 in the probability density function f(x1) (threshold determining step (2)).

Then a perimeter was used to perform the test result acquiring step (3) for obtaining a test result indicating whether or not a result greater than or equal to 21 dB was obtained in the first visual field test. The obtained result indicated that the test subject could not recognize the visual target.

Because a test result greater than or equal to 21 dB was not obtained, in the second probability density function acquiring step (4), the probability density function f(x2) was obtained by removing the probability density values greater than or equal to 21 dB from the probability density function f(x1).

FIG. 7(b) is a plot of the probability density function f(x2) after the first visual field test in Working Example 2.

Then the determining step (5) was performed to determine whether or not the standard deviation σ of the probability density function f(x2) had fallen below the predetermined value 3.9 dB (=(−0.1)*abs(20−19)+4.0). It was determined that the standard deviation σ did not fall below 3.9 dB in the first visual field test.

Second Round

The steps (2), (3), (4), and (5) were repeated in order.

More specifically, the stimulation threshold t2 was set to 15 dB from within the range of x2 in the probability density function f(x2) (stimulation threshold determining step (2)).

Then a perimeter was used to perform the test result acquiring step (3) for obtaining a test result indicating whether or not a result greater than or equal to 15 dB was obtained in the second visual field test. The obtained result indicated that the test subject could not recognize the visual target.

Because a test result greater than or equal to 15 dB was not obtained, in the second probability density function acquiring step (4), the probability density function f(x3) was obtained by removing the probability density values greater than or equal to 15 dB from the probability density function f(x2).

FIG. 7(c) is a plot of the probability density function f(x3) after the second visual field test in Working Example 2.

Then the determining step (5) was performed to determine whether or not the standard deviation σ of the probability density function f(x3) had fallen below the predetermined value 3.3 dB (=(−0.1)*abs(20−13)+4.0). It was determined that the standard deviation σ did not fall below 3.3 dB in the second visual field test either.

Third Round

The steps (2), (3), (4), and (5) were again repeated in order.

More specifically, the stimulation threshold t3 was set to 4 dB from within the range of x3 in the probability density function f(x3) (stimulation threshold determining step (2)).

Then a perimeter was used to perform the test result acquiring step (3) for obtaining a test result indicating whether or not a result greater than or equal to 4 dB was obtained in the third visual field test. The obtained result indicated that the test subject recognized the visual target.

Because a test result greater than or equal to 4 dB was not obtained, in the second probability density function acquiring step (4), the probability density function f(x4) was obtained by removing the probability density values greater than or equal to 4 dB from the probability density function f(x3).

FIG. 7(d) is a plot of the probability density function f(x4) after the third visual field test in Working Example 2.

Then the determining step (5) was performed to determine whether or not the standard deviation σ of the probability density function f(x4) had fallen below the predetermined value 2.0 dB (=(−0.1)*abs(20−0)+4.0). It was then determined that the standard deviation σ had fallen below 2.0 dB. The value of x4 having the highest probability density in the probability density function f(x4) was 0 dB.

The test value ultimately obtained through the above steps was 0 dB, and the visual field test was then ended.

Working Example 3

A test subject C was subjected to a visual field test using the visual field test device of the present embodiment.

The first probability density function acquiring step (1) was performed using the items "Age: 40", "Test coordinates: [−27,−3]" and "History of glaucoma: yes (ongoing)" acquired from information regarding the test subject C.

Figure 8:
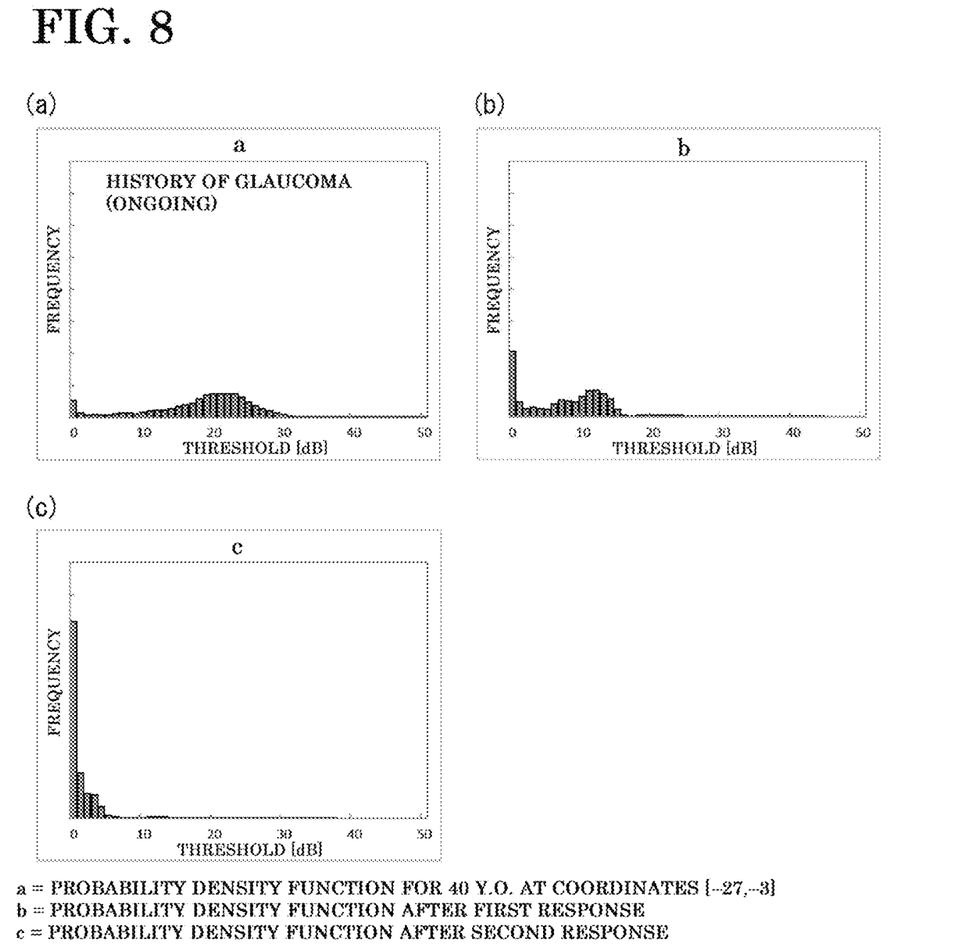

FIG. 8(a) is a plot of the probability density function f(x1) in the case where "Age: 40", "Test coordinates: [−27,−3]", and "History of glaucoma: yes (ongoing)" were selected in Working Example 3. FIG. 8(a) is the same as FIG. 4(b), but is reused to facilitate a comparison with FIGS. 8(b) and (c).

First Round

The stimulation threshold t1 was set to 15 dB from within the range of x1 in the probability density function f(x1) (stimulation threshold determining step (2)).

Then a perimeter was used to perform the test result acquiring step (3) for obtaining a test result indicating whether or not a result greater than or equal to 15 dB was obtained in the first visual field test. The obtained result indicated that the test subject could not recognize the visual target.

Because a test result greater than or equal to 15 dB was not obtained, in the second probability density function acquiring step (4), the probability density function f(x2) was obtained by removing the probability density values greater than or equal to 15 dB from the probability density function f(x1).

FIG. 8(b) is a plot of the probability density function f(x2) after the first visual field test in Working Example 3.

Then the determining step (5) was performed to determine whether or not the standard deviation σ of the probability density function f(x2) had fallen below the predetermined value 2.0 dB (=(−0.1)*abs(20−0)+4.0). It was determined that the standard deviation σ did not fall below 2.0 dB in the first visual field test.

Second Round

The steps (2), (3), (4), and (5) were repeated in order.

More specifically, the stimulation threshold t2 was set to 5 dB from within the range of x2 in the probability density function f(x2) (stimulation threshold determining step (2)).

Then a perimeter was used to perform the test result acquiring step (3) for obtaining a test result indicating whether or not a result greater than or equal to 5 dB was obtained in the second visual field test. The obtained result indicated that the test subject could not recognize the visual target.

Because a test result greater than or equal to 5 dB was not obtained, in the second probability density function acquiring step (4), the probability density function f(x3) was obtained by removing the probability density values greater than or equal to 5 dB from the probability density function f(x2).

FIG. 8(c) is a plot of the probability density function f(x3) after the second visual field test in Working Example 3.

Then the determining step (5) was performed to determine whether or not the standard deviation σ of the probability density function f(x3) had fallen below the predetermined value 2.0 dB (=(−0.1)*abs(20−0)+4.0). It was then determined that the standard deviation σ had fallen below 2.0 dB. The value of x3 having the highest probability density in the probability density function f(x3) was 0 dB.

The test value ultimately obtained through the above steps was 0 dB, and the visual field test was then ended.

As described above, according to these working examples, it is possible to provide a visual field test device, a method of controlling the same, and a visual field test program that can shorten the time required for a visual field test while also obtaining an accurate test value.

The invention claimed is:

1. A visual field test device comprising:
   a first probability density function acquisition unit configured to perform a step (1) of obtaining a probability density function f(x1) for a result value x1 obtained in a first visual field test, the probability density function f(x1) being a probability density function under at least two conditions regarding a test subject from among the number of years since a last test, an age, test coordinates, a history of illness, an illness name, an disease stage, an estimated threshold used in a past visual field test, and an indicator of a reliability of a past visual field test result;
   a stimulation threshold determination unit configured to perform a step (2) of setting a stimulation threshold t1 to a value in a range of x1 in the probability density function f(x1);
   a test result acquisition unit configured to perform a step (3) of obtaining a test result indicating whether or not a result greater than or equal to t1 was obtained in the first visual field test;
   a second probability density function acquisition unit configured to perform a step (4) of, if a test result greater than or equal to t1 is obtained, obtaining a probability density function f(x2) by removing probability density values that are less than t1 from the probability density function f(x1), and if a test result greater than or equal to t1 is not obtained, obtaining the probability density function f(x2) by removing probability density values that are greater than or equal to t1 from the probability density function f(x1); and
   a determination unit configured to perform a step (5) of determining whether or not a standard deviation σ of the probability density function f(x2) has fallen below a predetermined value,
   wherein if the determination unit determines that the standard deviation σ has fallen below the predetermined value, a value of x2 having a highest probability density in the probability density function f(x2) is deemed to be a test value, and testing is ended, and
   if the determination unit determines that the standard deviation σ has not fallen below the predetermined value, the first visual field test is replaced with a second visual field test, x2 is replaced with x3, x1 is replaced with x2, the stimulation threshold t1 is replaced with a stimulation threshold t2, and the second probability density function acquiring step is replaced with a third probability density function acquiring step, and the stimulation threshold determination unit, the test result acquisition unit, the second probability density function acquisition unit, and the determination unit repeat the steps (2), (3), (4), and (5) until the standard deviation σ of a probability density function f(x3) obtained by removing probability density values according to a test result has fallen below the predetermined value.

2. The visual field test device according to claim 1, wherein the test result acquisition unit is a perimeter.

3. The visual field test device according to claim 1, wherein in the second probability density function acquisition unit, probability density values are removed by multiplying the probability density function f(x1) by a response function.

4. The visual field test device according to claim 1, wherein the predetermined value used in the determination performed by the determination unit regarding the standard deviation σ is a value in a range of 1.0 to 3.5 dB.

5. A method of controlling a visual field test device such that
   a first probability density function acquisition unit performs a first probability density function acquiring step (1) of obtaining a probability density function f(x1) for a result value x1 obtained in a first visual field test, the probability density function f(x1) being a probability density function under at least two conditions regarding a test subject from among the number of years since a last test, an age, test coordinates, a history of illness, an illness name, an disease stage, an estimated threshold used in a past visual field test, and an indicator of a reliability of a past visual field test result;

a stimulation threshold determination unit performs a stimulation threshold determining step (2) of setting a stimulation threshold t1 to a value in a range of x1 in the probability density function f(x1);

a test result acquisition unit performs a test result acquiring step (3) of obtaining a test result indicating whether or not a result greater than or equal to t1 was obtained in the first visual field test;

a second probability density function acquisition unit performs a second probability density function acquisition step (4) of, if a test result greater than or equal to t1 is obtained, obtaining a probability density function f(x2) by removing probability density values that are less than t1 from the probability density function f(x1), and if a test result greater than or equal to t1 is not obtained, obtaining the probability density function f(x2) by removing probability density values that are greater than or equal to t1 from the probability density function f(x1); and a determination unit performs a determining step (5) of determining whether or not a standard deviation σ of the probability density function f(x2) has fallen below a predetermined value, wherein if it is determined in the step (5) that the standard deviation σ has fallen below the predetermined value, a value of x2 having a highest probability density in the probability density function f(x2) is deemed to be a test value, and testing is ended, and if it is determined in the step (5) that the standard deviation σ has not fallen below the predetermined value, the first visual field test is replaced with a second visual field test, x2 is replaced with x3, x1 is replaced with x2, the stimulation threshold t1 is replaced with a stimulation threshold t2, and the second probability density function acquiring step is replaced with a third probability density function acquiring step, and the stimulation threshold determination unit, the test result acquisition unit, the second probability density function acquisition unit, and the determination unit repeat the steps (2), (3), (4), and (5) until the standard deviation σ of a probability density function f(x3) obtained by removing probability density values according to a test result has fallen below the predetermined value.

6. The method of controlling a visual field test device according to claim 5,
wherein the steps (2), (3), (4), and (5) are performed three times or fewer.

7. The method of controlling a visual field test device according to claim 5,
wherein in the step (4), probability density values are removed by multiplying the probability density function f(x1) by a response function.

8. The method of controlling a visual field test device according to claim 5,
wherein the predetermined value used in the determination performed in the step (5) regarding the standard deviation σ is a value in a range of 1.0 to 3.5 dB.

9. A visual field test program that causes a computer device to function as:

a first probability density function acquisition unit configured to perform a step (1) of obtaining a probability density function f(x1) for a result value x1 obtained in a first visual field test, the probability density function f(x1) being a probability density function under at least two conditions regarding a test subject from among the number of years since a last test, an age, test coordinates, a history of illness, an illness name, an disease stage, an estimated threshold used in a past visual field test, and an indicator of a reliability of a past visual field test result;

a stimulation threshold determination unit configured to perform a step (2) of setting a stimulation threshold t1 to a value in a range of x1 in the probability density function f(x1);

a test result acquisition unit configured to perform a step (3) of obtaining a test result indicating whether or not a result greater than or equal to t1 was obtained in the first visual field test;

a second probability density function acquisition unit configured to perform a step (4) of, if a test result greater than or equal to t1 is obtained, obtaining a probability density function f(x2) by removing probability density values that are less than t1 from the probability density function f(x1), and if a test result greater than or equal to t1 is not obtained, obtaining the probability density function f(x2) by removing probability density values that are greater than or equal to t1 from the probability density function f(x1); and a determination unit configured to perform a step (5) of determining whether or not a standard deviation σ of the probability density function f(x2) has fallen below a predetermined value, wherein if the determination unit determines that the standard deviation σ has fallen below the predetermined value, a value of x2 having a highest probability density in the probability density function f(x2) is deemed to be a test value, and testing is ended, and if the determination unit determines that the standard deviation σ has not fallen below the predetermined value, the first visual field test is replaced with a second visual field test, x2 is replaced with x3, x1 is replaced with x2, the stimulation threshold t1 is replaced with a stimulation threshold t2, and the second probability density function acquiring step is replaced with a third probability density function acquiring step, and the stimulation threshold determination unit, the test result acquisition unit, the second probability density function acquisition unit, and the determination unit repeat the steps (2), (3), (4), and (5) until the standard deviation σ of a probability density function f(x3) obtained by removing probability density values according to a test result has fallen below the predetermined value.

10. The visual field test program according to claim 9,
wherein the steps (2), (3), (4), and (5) are performed three times or fewer.

11. The visual field test program according to claim 9,
wherein in the step (4), probability density values are removed by multiplying the probability density function f(x1) by a response function.

12. The visual field test program according to claim 9,
wherein the predetermined value used in the determination performed in the step (5) regarding the standard deviation σ is a value in a range of 1.0 to 3.5 dB.

* * * * *